United States Patent
Brancaccio et al.

(10) Patent No.: US 11,583,209 B2
(45) Date of Patent: Feb. 21, 2023

(54) SYSTEM AND METHOD FOR A PERSONALIZED REMINDER WITH INTELLIGENT SELF-MONITORING

(71) Applicant: Revibe Technologies, Inc., Wake Forest, NC (US)

(72) Inventors: Richard Brancaccio, Wake Forest, NC (US); Christopher Guidry, Wake Forest, NC (US); David Vaughn, Wake Forest, NC (US)

(*) Notice: Subject to any disclaimer, the term of this patent is extended or adjusted under 35 U.S.C. 154(b) by 0 days.

(21) Appl. No.: 17/381,288

(22) Filed: Jul. 21, 2021

(65) Prior Publication Data
US 2021/0350921 A1    Nov. 11, 2021

Related U.S. Application Data

(63) Continuation-in-part of application No. 15/898,492, filed on Feb. 17, 2018, now Pat. No. 11,191,433.

(51) Int. Cl.
| | | |
|---|---|---|
| *A61B 5/11* | (2006.01) | |
| *G06F 1/16* | (2006.01) | |
| *G06N 20/00* | (2019.01) | |

(52) U.S. Cl.
CPC ............ *A61B 5/1118* (2013.01); *G06F 1/163* (2013.01); *G06N 20/00* (2019.01)

(58) Field of Classification Search
None
See application file for complete search history.

(56) References Cited

U.S. PATENT DOCUMENTS

| | | | |
|---|---|---|---|
| 5,402,108 A | 3/1995 | Tabin et al. | |
| 5,954,630 A | 9/1999 | Masaki et al. | |
| 6,461,316 B1 | 10/2002 | Lee et al. | |
| 6,558,165 B1 | 5/2003 | Curry et al. | |
| 9,529,385 B2* | 12/2016 | Connor | G09B 19/0092 |
| 10,181,251 B2* | 1/2019 | Gao | G08B 21/24 |
| 2004/0115603 A1 | 6/2004 | Reynolds | |
| 2007/0049788 A1 | 3/2007 | Kalinowski et al. | |
| 2007/0284401 A1 | 12/2007 | Hilliard | |
| 2008/0288023 A1* | 11/2008 | John | G16H 20/40 607/59 |
| 2011/0128151 A1* | 6/2011 | Asad | A61B 5/168 340/573.1 |

(Continued)

FOREIGN PATENT DOCUMENTS

| | | |
|---|---|---|
| CA | 2039671 A1 | 10/1991 |
| DE | 102010026781 A1 | 1/2012 |

OTHER PUBLICATIONS

Looking At The Body: Automatic Analysis of Body Gestures and Self-Adaptors in Psychological Distress—IEEE (Year: 2015).*

(Continued)

*Primary Examiner* — Mandrita Brahmachari

(57) ABSTRACT

The system and method disclosed utilizes a wearable device to collect data generated pursuant to user's kinesthetic movement. The instant innovation filters and cleans the data, then slices the data into subsets. The subsets are analyzed with a Machine Learning algorithm to identify signal patterns indicative of statistically significant behavioral metrics, and the instant innovation returns insights based in part on relationships between said behavioral metrics. These insights are returned to an observer in the form of a report.

12 Claims, 6 Drawing Sheets

(56) References Cited

U.S. PATENT DOCUMENTS

| | | | |
|---|---|---|---|
| 2012/0244503 A1* | 9/2012 | Neveldine | G09B 19/00 |
| | | | 434/236 |
| 2013/0110895 A1 | 5/2013 | Valentino et al. | |
| 2014/0245789 A1* | 9/2014 | Proud | A61B 5/681 |
| | | | 63/1.13 |
| 2014/0370471 A1 | 12/2014 | Brancaccio | |
| 2015/0141080 A1* | 5/2015 | Standing | G06F 3/0445 |
| | | | 455/566 |
| 2015/0288797 A1* | 10/2015 | Vincent | G16H 10/60 |
| | | | 455/404.2 |
| 2016/0042289 A1* | 2/2016 | Poola | H04L 67/10 |
| | | | 706/52 |
| 2016/0082222 A1* | 3/2016 | Garcia Molina | A61M 21/02 |
| | | | 600/27 |
| 2016/0161985 A1* | 6/2016 | Zhang | A61B 5/02055 |
| | | | 600/595 |
| 2016/0287166 A1* | 10/2016 | Tran | A61B 5/74 |
| 2016/0310341 A1* | 10/2016 | Yu | A61B 5/7445 |
| 2017/0228121 A1* | 8/2017 | Wosk | G04G 9/0064 |
| 2017/0293727 A1* | 10/2017 | Klaassen | G16H 40/67 |
| 2017/0296116 A1* | 10/2017 | McCarthy | A61B 5/112 |
| 2018/0188694 A1* | 7/2018 | Wu | G04G 99/006 |
| 2018/0286429 A1* | 10/2018 | Bostick | G06F 40/30 |

OTHER PUBLICATIONS

Looking At The Body: Automatic Analysis of Body Gestures and Self-Adaptors in Psychological Distress—Jaiswal et al. (Year: 2016).*
Corresponding U.S. Appl. No. 17/521,954 Office Action dated Jul. 14, 2022.

* cited by examiner

SYSTEM AND METHOD FOR A PERSONALIZED REMINDER WITH INTELLIGENT SELF-MONITORING

CLAIM TO PRIORITY

This application claims under 35 U. S.C. § 120, the benefit of the application Ser. No. 15/898,492, filed Feb. 17, 2018, titled "Apparatus and Method for a Personalized Reminder with Intelligent Self-Monitoring," which is hereby incorporated by reference in its entirety.

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever.

BACKGROUND

Wearable systems that incorporate sensors to determine physical parameters of a wearer are known and present in the marketplace. Sensors indicating position, heartrate, movement in exercise positions, among other parameters collect data about the user and provide feedback to a user in realtime. Such systems may also be connected through a data communications channel to a computer system having analytical software to review collected data and provide analysis to a user or third party on parameters that are of interest to the user. With appropriately miniaturized electronics, the sensors may be located in a smaller portion of the user's body such as the ear. The data collected may be used to assist users understanding about their physical state during exercise, work, sleep, or other activities.

Feedback may also be provided to the user through a wearable device. The feedback may be through elements installed within the wearable device or may be sent to a mobile or WIFI connected device that is in data communication with the wearable device. The feedback may form a portion of a user's medical record, or may be used to assist the wearer in keeping physical parameters within certain specified ranges during physical activity.

The wearable device may also be active to determine whether a user was engaged in undesirable behavior while the device is being worn. The wearable device may actively monitor the user to collect and store information about the user's activities at certain time periods and/or when the user's activity level exceeds pre-configured thresholds for specified activities. If the determined intensity of activity exceeds the established threshold, the device could activate the feedback mechanism in an attempt to provide correction for the user to follow so as to change the user's behavior. However, currently available wearable devices do not often provide the user with the capability to interact with the feedback capability of the wearable device to provide customized feedback and corrective capability.

BRIEF DESCRIPTION OF THE DRAWINGS

Certain illustrative embodiments illustrating organization and method of operation, together with objects and advantages may be best understood by reference to the detailed description that follows taken in conjunction with the accompanying drawings in which.

DETAILED DESCRIPTION

Figure 1:
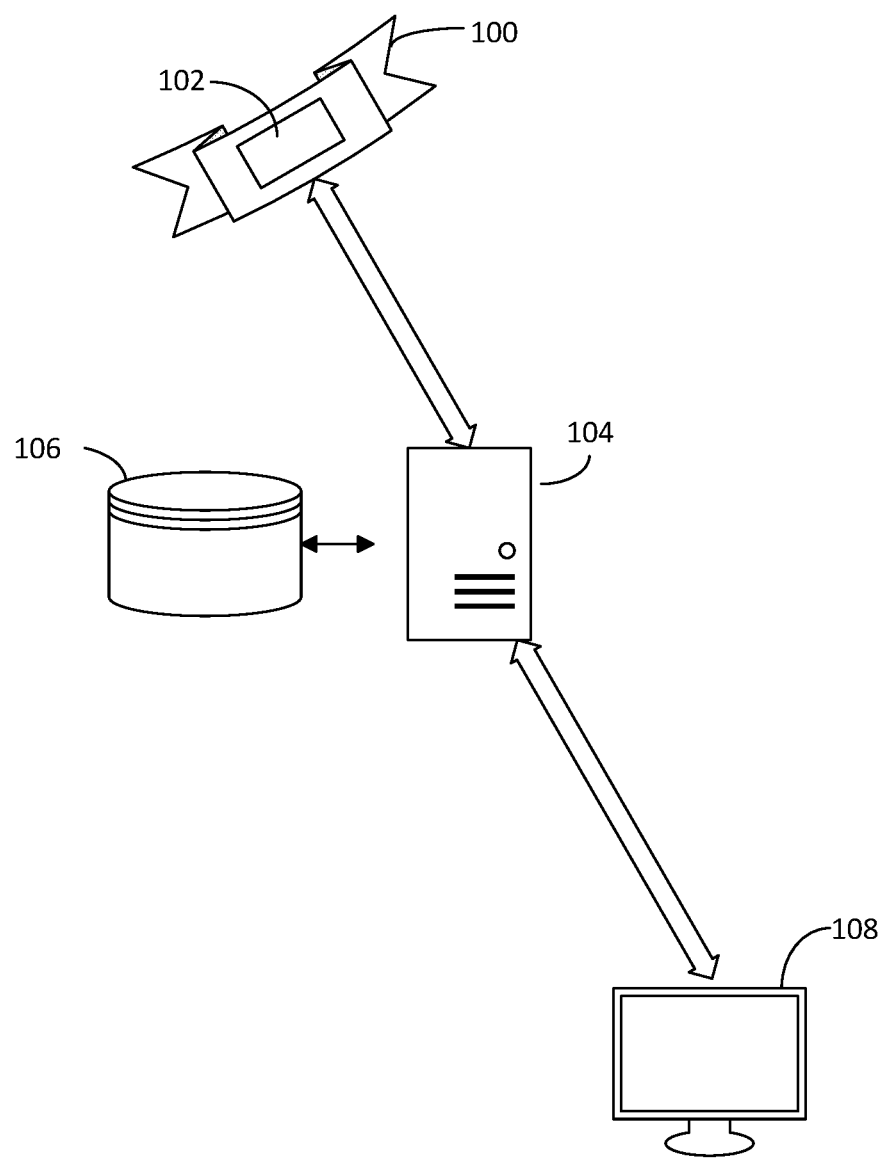
FIG. 1 is a view of a system configuration consistent with certain embodiments of the present invention.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

Reference throughout this document to "On-task Behavior", or similar terms "Focused Behavior", "Focus", or "Attention" refers to any behaviors deemed appropriate or desired by the user in the context of using a reminder device. In a non-limiting example, if a user desires to demonstrate better attention, listening skills or work completion, these behaviors may be deemed as "On-Task Behavior".

Reference throughout this document to "Off-task Behavior" refers to behaviors deemed inappropriate or not desired by the user in the context of using a reminder device.

Reference throughout this document to "Fidgeting" or "Fidget behavior", refers to how frequently an individual tends to shuffle, wiggle or engage in other 'still or seated movements', commonly seen in children and adults with Attention Deficit, Hyperactivity Disorder, also including but not limited to wrist and hand movements, and including hand flapping, hand-wringing and other stereotyped behaviors commonly associated with Autism stimming, that may affect the person's productive behavior and/or be related to their ability to quietly sit or stand and attend or focus on a given task.

In an embodiment with regard to these reported behaviors, users of the invention described in this document may utilize a well-known technique called Self-Monitoring, or SM. Self-Monitoring is a well-documented, highly researched behavioral intervention which has been shown to be a highly effective means of increasing desired behaviors and decreasing undesired behaviors. Previously, however, there has been a lack of integration between SM and technology. This document presents a system and method to operatively utilize SM to improve the on-task behavior, focus and/or attention of a user by precisely adjusting factors that adjust the frequency, intensity and patterning of reminder prompts through various stimuli, such as a tactile vibration, audible tone, visual stimulus, or other stimuli that may form a reminder prompt, defined as, in a non-limiting example, "F-factors".

In this embodiment, the system and method utilizes a pool of research-based data tables to pseudorandomize meta-cognitive reminders. Such reminders encourage users to be more cognizant and aware of their own behaviors. This self-awareness of personal behaviors may in-turn help increase an individual's ability to stay on-task. By providing a platform to query a user regarding their own on-task and off-task behaviors, as well as to collect and compile in order to intelligently harness this data, the system and method described may be able to impart change through targeted reminders driven by actual, longitudinal collected user data.

In an embodiment, an algorithm may determine when and how to adjust reminders based-on user input in regards to self-reported on-task and off-task behaviors. Over time, this system progressively gathers user data and learns details of a user's activity and habits, and becomes more and more attuned to the user's needs. The device containing the sensors and that provides prompt reminders to a user, is worn by the user. In a non-limiting example, the device may sample the user's behavior multiple times per second, collecting measurements from each sampling period to aggregate data over time for analysis, operations, and to provide a prompt to the user when the system determines that any change that merits a reminder to the user has occurred. Based-on collected and historically aggregated data that illumine user behaviors, a computer software module may be operative to analyze the current collected and historically aggregated data to determine the most appropriate minimum and maximum values for prompt timing to ensure maximum on-task behavior with a high degree of confidence in the results of the analysis. The data analysis may also serve to minimize over-prompting to keep meaningfulness high, where meaningfulness is defined as of benefit to a user in accomplishing a desired goal, and habituation to repeated prompting low.

In an embodiment, while collecting data, it is imperative to categorize the collected information into useful segments. If not properly categorized, the data may become less relevant due to situational constraints. In a non-limiting example, if an individual desires to actively track the ability to listen to a teacher or lesson, but from time to time is sitting at a cafeteria table during lunch instead of being engaged in listening to a teacher or lesson, then the information collected is less relevant. Even different environments that are more relevant tend to net differing levels of interest, attention and on/off-task behaviors. For this reason, a scheduling component is incorporated into the system and method to intelligently collect and organize data. In a non-limiting example, data will not be collected during certain, pre-determined periods of time, such as during lunch, physical education, or other time periods as configured during the operation setup of the device in which the user may be distracted or not dedicated to a desired task, but may be collected and then leveraged in a unique fashion during other time periods. In a non-limiting example, reminders may also be amplified, as needed, in certain key environments. To do this, a calendar or schedule is initially completed by the user, including start and end times to provide the system with insight into a user's established schedule. The reminder device component of the system includes a real-time clock feature which auto-updates in order to correctly utilize schedule events and engage reminders.

In an embodiment, the system and method may actively collect a user's reported behaviors in order to continually optimize each of several focus factors, previously defined as "F factors". Based on a user's reported behaviors to a posed question, such as "When you feel this vibrate, ask yourself if you were on-task or off-task—press user response button 2 times for on-task and 1 time for off-task", a computer algorithm is operative to determine whether or not to increase, decrease or leave unchanged the aforementioned F-factors in order to continually provide as much prompting as necessary to improve users on-task behaviors, but as little prompting so as not to become burdensome or to force user to habituate. Habituation is further staved-off by pseudo-randomizing one or more of the F factors.

In an exemplary embodiment, the system and method described comprises a device, preferably worn on the wrist although this should in no way be considered limiting as the device may be worn on any appendage or as a necklace, headband, or other fashion-conscious garment. The device may have a processor that incorporates a machine learning algorithm to determine alternations in vibrations and changes in the pitch of generated tones to provide reminders to a wearer to remain focused on an activity. In this exemplary embodiment, the machine learning algorithm is operative to determine the best times to remind the wearer based upon user action in response to the user history of responses to reminder prompts. The machine learning algorithm may also take into account the user's daily or weekly schedule of activities and tasks in determining when to send a reminder prompt. The wearer's schedule may be added to provide more directed collection of data with regard to on/off task time percentage, goals of the user, and sending an automatic email report on user activity to a caregiver, parent, health care professional, or other authority associated with the user.

In an alternative exemplary embodiment, a wearer, in some instances a child, may receive additional mandatory remind times when they must respond to a device vibration and/or tone by tapping the device. Device vibrations may indicate states or timing through alternative vibrations, tones, or other distinguishing tactile or audible actions. The machine learning algorithm associated with the device may modify vibrations, tones, sequences, intensity and other prompt actions based upon user response. The vibrations and frequencies of the tones may change based upon patterns of response from the user, thus learning the habits of the user in terms of response to prompts.

In an embodiment, the instant innovation includes a wearable device used to collect data generated pursuant to user's kinesthetic movement. The instant innovation filters and cleans the data, then slices the data into subsets. The subsets are analyzed with a Machine Learning algorithm to identify signal patterns indicative of statistically significant behavioral metrics, and the instant innovation returns insights based in part on relationships between said behavioral metrics. These insights are returned to an observer in the form of a report.

In an embodiment, the device may be in communication with a system server for reporting, updates, and other communications. A detection engine may receive sensor data from the device and may filter the received data for desired potential data while discarding data determined to be noise or otherwise unwanted data. The instant innovation may utilize an on-board quantization processor, in a non-limiting example, to send desired data to and/or from one or more mobile devices. The instant innovation may utilize a communications protocol such as, but not limited to, Bluetooth as incorporated into a device to send such desired data to and/or from one or more mobile or smart devices. In an embodiment, the instant innovation may employ a base server, such as, by way of non-limiting example, a Lambda Data Base Server to slice the desired data into smaller data chunks for ease of processing and analysis. The instant innovation may store a copy of all desired data upon one or more servers.

The innovation described herein may use one or more Machine Learning Algorithms associated with one or more processors to scan and analyze the desired data for signal patterns that help the instant innovation to identify kinesthetic movement that may characterize any cyclic, repetitive non-academically functional behavior associated with ADHD, Autism, or other motor-related medical conditions. In a non-limiting example, such cyclic, repetitive non-academically functional behaviors may be quantified or identified as fidget behaviors. In an embodiment the instant innovation identifies and distinguishes signal patterns associated with a user's sitting and standing behavior to determine whether cyclic, repetitive non-academically functional behaviors, such as, in a non-limiting example, fidget behaviors are present. Signal patterns associated with a user's sitting are distinguished between fidgeting and non-fidgeting behavior. The instant innovation characterizes analyzed sitting fidgeting behavior as one or more of several distinctive types of behavior including, by way of non-limiting example, drumming, jumping, tapping, hopping, and/or rocking among other kinesthetic movements.

In an embodiment, the characterized behavior may also include specific non-limiting categories including handwriting, in which the innovation determines the rate at which the user writes words, which, in a non-limiting example, may be measured as words written per minute, or may be quantified in any other manner that determines the rate of completed words in a given period of time. The system may also quantify such motions as hand raising, in which the innovation determines the rate at which the user raises a hand during a given time period. Additionally, the system may quantify turning behavior, in which the innovation determines the rate at which the user turns to speak or otherwise interact with peers sitting nearby, where the rate may be quantified as the number of interactions in a given period of time.

Signal patterns associated with a user's standing fidget behavior are distinguished by identifying when a user is standing still or walking while standing. The system may also quantify when a user is running as opposed to standing behaviors. When the instant innovation as described herein determines that standing behavior is characterized by walking or running, the instant innovation performs and stores one or more step counts, as well as collecting information on when a user starts and stops either walking or running, and stores this collected data for later analysis.

The system may also collect and share information such as the overall 'fidget minutes' captured during a given time period and store this information as metrics on the actions of a user during periods of recorded fidget behavior. During periods when fidget behavior has been detected, the fidget behavior actions and measured data that are captured may include all fidget behavior metrics in either standing or seated positions, and a count of steps and/or indication of calories expended during walking, running, or other standing or sitting fidget behavior.

In additional embodiments, the device may track additional kinesthetic movement where an individual is largely stationary, such as in a seated position. Such stationary movement (fidgeting, etc.) data may be collected and tracked to identify and quantify the user's various seated behaviors in addition to any standing fidget behaviors. Tracking fidgeting behaviors of all types permits the system and method of the instant innovation to perform updates and changes to the prompt generation algorithm based upon determining various states of physical excitation and activity, and/or of physical response or reaction time, as well as to situations in which the user does not respond to a prompt. In additional embodiments, the system and method may modify the prompt generation algorithm based upon a user's class scheduling, if the user is a student, or based upon the previous day and/or week's performance on responses to prompts captured and stored in the aggregated history data. The system may analyze the captured data to determine prompts to send that may assist a user in modifying or minimizing fidget behaviors of all types and transmit such modified and updated prompts to the wearable device for action by the user.

In an embodiment, the system also utilizes trends in individual user's behaviors to prescribe suggestions, by combining research-based interventions with actual user behaviors measured over time, for the duration and intensity of said research-based behavioral interventions. This allows information to be presented to one or more observers including teachers, supervisors, other authority figures, or the users themselves with individualized recommendations for each user in each environment such as classes, job functions, or any other environment in which performance is expected and required.

In an embodiment, the instant innovation enables a personalized insight engine by creation, maintenance and analysis of one or more individual user databases. The instant innovation performs multiple queries for specific metrics above key P-values. As defined herein, a P-value represents the probability of obtaining results at least as extreme as the observed results of a statistical hypothesis test, assuming the null hypothesis is correct. In instances where the algorithm of the instant innovation determines that the presence of specific metrics above key P-values satisfies criteria for one or more specific behavioral relationships, the instant innovation may create and send one or more reports to the user, teacher, supervisor or other observer. Such one or more reports may be auto-generated text descriptions revealing one or more behavioral insights that may be ascribed to the user of the device. In a non-limiting example, such text description may read, "It was noted that when Child 3 has the opportunity to take at least 44,000 steps before Tuesday in a given week, Child 3's hourly rate of Fidgeting for the rest of the week has been shown to decrease by 33 percent on average when compared to weeks when they've not had this opportunity." This text may be transmitted to the user, teacher, doctor or clinician, or other observer if the insight engine algorithm of the instant innovation has determined that sufficient criteria have been met to enable the transmission of such insights based upon analysis of the individual user database. In other non-limiting examples, the instant innovation may return a text description such as, "It was noted that when Child 2 has the opportunity to take at least 15,000 steps before lunch each day, Child 2's Attention Span rate for the rest of the day has been shown to improve by 5 minutes on average when compared to days when they've not had this opportunity," or "It was noted that when Child 1 has the opportunity to fidget for at least 15 minutes before 10 am each day, Child 1's Focus Rate for the rest of the day has been shown to be 30% higher than on days when they've not had this opportunity."

Walking/Running/Fidgeting are also quantified by advanced motion sensors and tracked over time in order to determine how active an individual may be, and whether or not their activity level is considered 'over-active' relative to both self and peers. The determination of activity level based upon these activities may then prompt an increase in the frequency of reminders or in the duration or composition of reminders, as necessary, based-on excessive levels of fidgeting as described above, to remind users to re-engage in their desired on-task behaviors.

The system implements all data collected (Self-Monitored responses, physical motions, schedule and environment) to make real-time on-the-fly changes to reminder prompt durations, frequency, amplitude and wavelength to both custom-tailor to the user's exact needs, so as not to over, or under, prompt, as well to provide a constantly unique prompt experience, which may help increase time on-task and reduce habituation.

Turning now to FIG. 1, this figure presents a view of a system configuration consistent with certain embodiments of the present invention. In an exemplary embodiment, the system and method comprises a device 100 that is worn by a user. One or more sensors, including but not limited to, motion sensors, may be incorporated into the device to collect motion data associated with the user. One or more prompt elements, including, but not limited to, elements that produce tactile, visual, auditory, or other prompts to catch the attention of the user are also included in the device 100. The device 100 may also incorporate a display element 102 that provides for visual information to be presented to the user at the determination of the system. The device 100 may also contain an RF, WIFI, Bluetooth, Bluetooth Low Energy (BLE), or other transmission protocols developed and released for use in wired or wireless data communication.

In an embodiment, the transmission capability may provide for connection and communication with a system server 104. The system server 104 may incorporate a plurality of software modules (not shown) operative to transmit commands and data to the device 100 and receive data from the device 100. The software modules may transmit prompt commands to the device 100, stimulating any of the tactile, visual, auditory, or other prompt elements to activate and provide a prompt to capture the user's attention. The user will sense the prompt and provide a response to the prompt by tapping or otherwise interacting with the device 100 to indicate whether the user is on-task or off-task at the time the prompt was noticed by the user. The response by the user may then be transmitted by the device 100 back to the server 104 where the user response may be stored in a database element 106 in a file dedicated to the user and containing all response and tracking data associated with each user. The server 104 may then communicate a report to a display or other interactive device 108 associated with a parent, teacher, healthcare professional, or other authority figure associated with the user. This informative report can be used to both inform as well as motivate the user by providing customized reporting on progress towards behavioral improvement, personalized goals or peer-based benchmarks; this can be presented to the user in the form of a customized report, animation/cartoon character, avatar or other modality. Progress from successful feedback to SM prompts may also be used to generate 'points', tokens, credits or the like in order to motivate the user by allowing them additional time, features, etc. for an in-application game, or a game external from the device application. The device and companion software can also utilize data garnered from the device to drive individualized recommendations, suggestions, and/or feedback, presented in a daily, weekly or monthly report.

Figure 2:
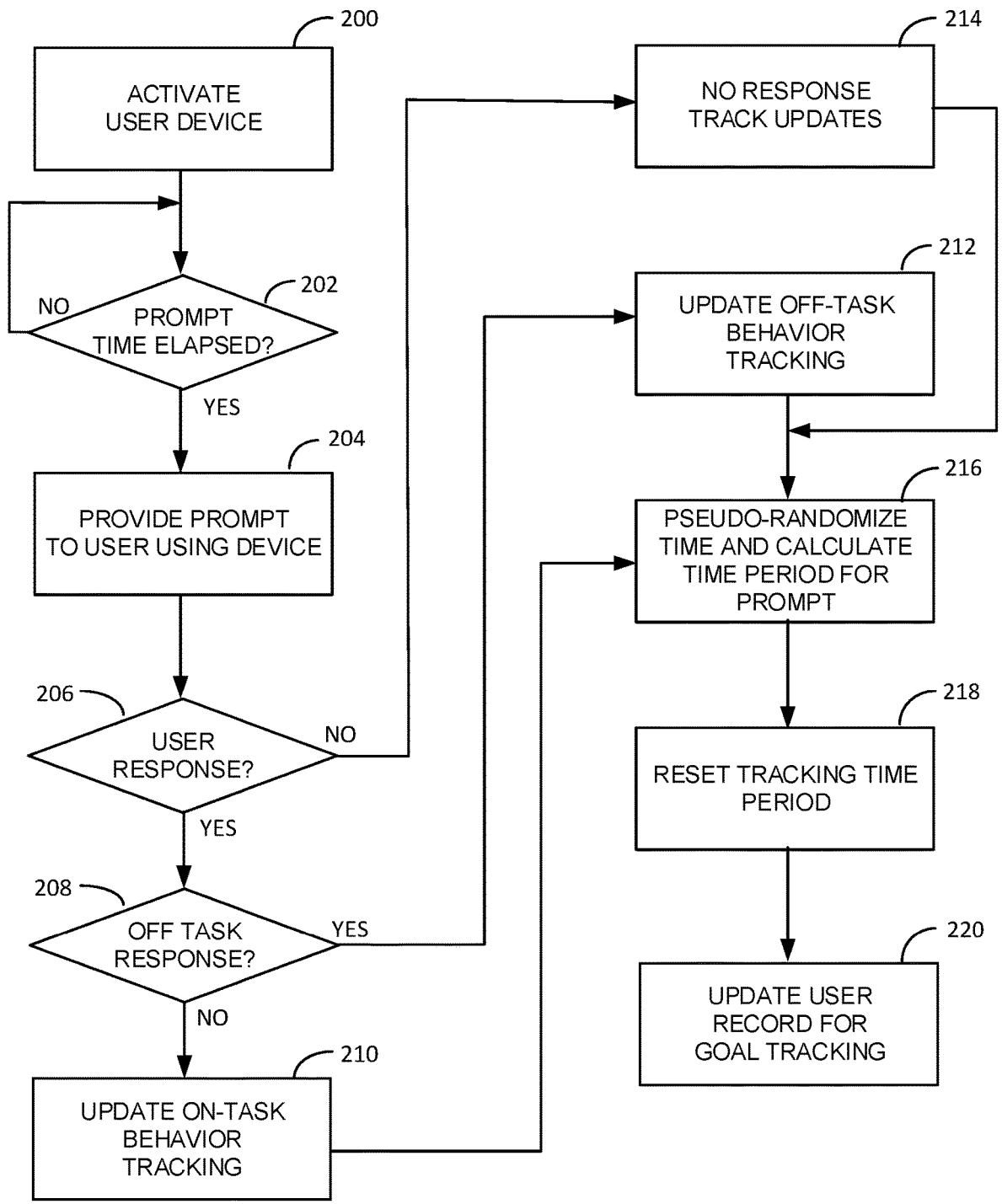
FIG. 2 is an operational flow diagram for pseudo-randomized operation consistent with certain embodiments of the present invention.

Turning now to FIG. 2, this figure presents an operational flow diagram for pseudo-randomized operation consistent with certain embodiments of the present invention. In an exemplary embodiment, the user attaches the device to their person and the system is activated by the user at 200. The device interrogates the internal prompt timing value transmitted from the server to the device at 202 and checks to determine if the prompt timing value has been exceeded.

At 204 the device has determined that the prompt timing value has been exceeded and initiates the prompt chosen by the user, whether tactile, auditory, visual, or other prompt indication. At 206 the device waits a pre-configured amount of time for a response to the prompt indication from the user. If the device receives a response from the user in the pre-configured amount of time permitted for the user to respond, at 208 the device reviews the response from the user to determine if the user is indicating they are on-task or off-task. If the user has indicated by the appropriate response that they were on-task at the time they received the prompt from the device, the device at 210 sends an indication of on-task behavior to the system server which is then active to update the user on-task tracking file in the database. If, however, the user has indicated, again by the appropriate response, that they were off task, the device at 212 sends an indication of off-task behavior to the system server which is then active to update the user off-task tracking file in the database.

At 214, when the user has not provided a response to the prompt transmitted by the device, the device sends an indication of a lack of response to the prompt to the system server which is then active to update the user no-response tracking file in the database.

Regardless of the response or lack of response to the prompt by the user, at 216 the system server is operable to create a new time period setting for the next prompt interval to be used by the device by activating a pseudo-randomization algorithm to calculate a new prompt time period utilizing tracked on and off task time percentage and the user's goals. At 218, the system server resets the prompt time period in the internal database and transmits this new time period value to the device. The device replaces the previous prompt time interval with the newly received prompt time interval and begins checking for elapsed time against the prompt time interval. At 220 the system updates the user record for goal tracking based upon the user response information.

Figure 3:
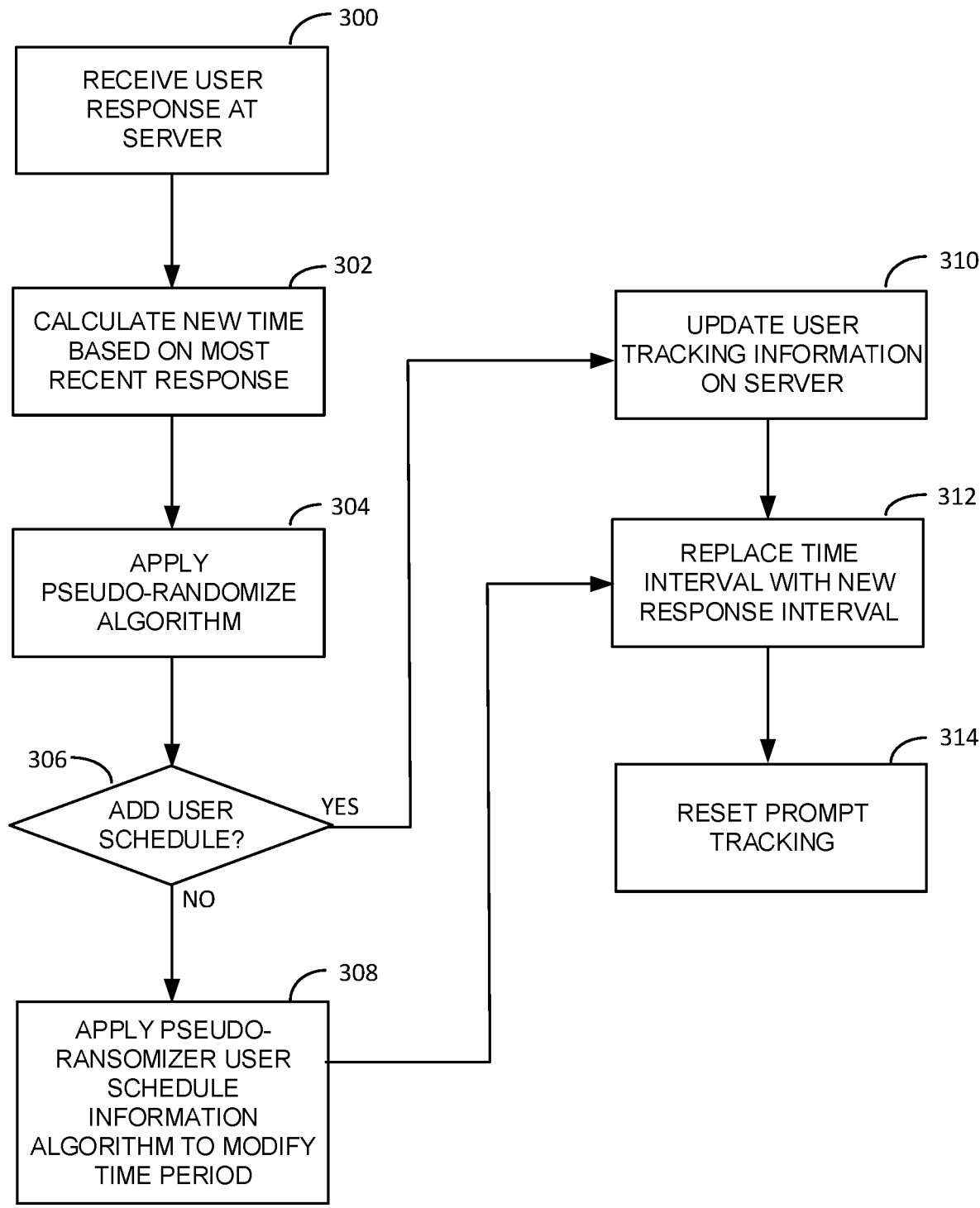
FIG. 3 is an operational flow diagram for prompts incorporated a user's schedule consistent with certain embodiments of the present invention.

Turning now to FIG. 3, this figure presents an operational flow diagram for prompts incorporated a user's schedule consistent with certain embodiments of the present invention. In an exemplary embodiment, at 300 the system server may receive a response from the device associated with a user. At 302 the system server tracking software module may be operable to calculate the time from the most recent response received from the user associated with the device. At 304, the system server is operable to create a new time period setting for the next prompt interval to be used by the device by activating a pseudo-randomization algorithm to calculate a new prompt time period utilizing on and off task time percentage and the user's goals. At 306, the system server determines whether the user's schedule is to be utilized in the calculation of a new prompt time period. If the user's schedule is to be utilized, at 308 the system server may take into account the user's schedule, special circumstances, previous response performance, and input these parameters into the pseudo-randomizer software module. The pseudo-randomizer module may then utilize these input parameters and initiate the pseudo-randomization algorithm to modify the response time period by determining the most appropriate minimum and maximum values for prompt timing to ensure maximum on-task behavior, while also minimizing over-prompting to keep meaningfulness high and habituation low. The new prompt time period calculated utilizing the user's schedule is used to update the user tracking information on the system server.

If the user's schedule is not to be used in the calculation of a new prompt time period, the system server simply updates the user tracking information with the new prompt time period that was calculated without input from the user's schedule at 310. At 312, the system server replaces the elapsed prompt time period with the newly calculated prompt time period and transmits the newly calculated prompt time period to the device to replace the prompt time period just elapsed. The system server then updates the database with all tracking information and resets the tracking information for the user at 314.

Figure 4:
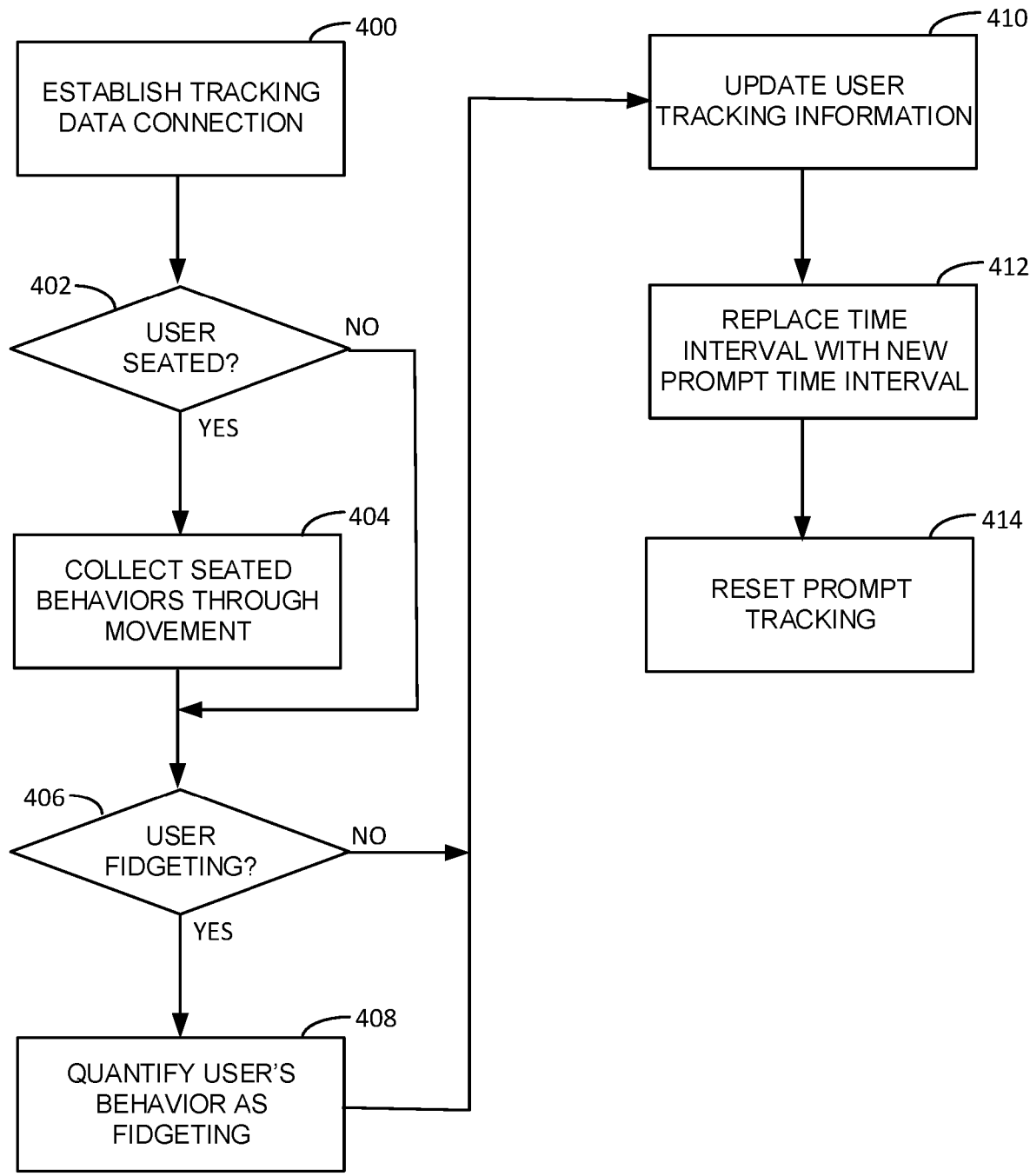
FIG. 4 is an operational flow diagram for detecting fidget behavior consistent with certain embodiments of the present invention.

Turning now to FIG. 4, this figure presents an operational flow diagram for detecting fidget behavior consistent with certain embodiments of the present invention. In this exemplary embodiment, the tracking information input by the user may be stored within the wearable device. The system server establishes a data communication connection with the device to establish a tracking connection between the device associated with a user and the system server at 400. The system server may transmit any tracking information stored within the server to a cloud-based storage facility, collect tracking information from the wearable device and transmit the collected tracking information to the cloud-based storage, or provide a real-time update of tracking information from the wearable device, through the server, and on to the cloud-based storage facility. The system server at 402 is active to determine that the user is seated by receiving and analyzing motion sensor data to determine the user's movement. If the user's movement is constrained to within a certain parameter set that indicates the user is not moving to a different physical position, not walking or running, the system server may determine that the user is seated. In an alternative embodiment, the system server at 406 may also be active to determine that a user is standing, hopping, or remaining in one spot for a period of time but performing fidgeting-type behaviors.

In an embodiment, the system is active to collect all data associated with a user, regardless of physical position, whether standing, seated, reclining, or in active motion. However, if the user is determined to be seated or remaining substantially in a single physical position by sensor data analysis, at 404 the system server is active to categorize collected data as associated with a localized physical position, either seated or standing, and collects all sensor data from the device as indicia of a user's fidgeting behaviors. At 406, the movement software module is operative to determine if the seated or standing behaviors of a user are indicative of fidgeting, as defined previously. If the collected behaviors indicate that the user is fidgeting at 408 the system server quantifies the user's movement as fidgeting and stores the sensor data along with an indication of fidgeting behavior and timing data associated with the length of time the user is exhibiting this fidgeting behavior. Whether the user's behavior is indicative of fidgeting, whether standing or seated, or not, the system server updates the tracking information associated with the user at 410. At 412, the system server calculates a new prompt time interval through a pseudo-randomization algorithm with an added parameter to account for fidgeting behavior and transmits the newly calculated prompt time interval to the device associated with the user. At 414, the system is operative to reset the prompt interval tracking to continue operation.

Figure 5:
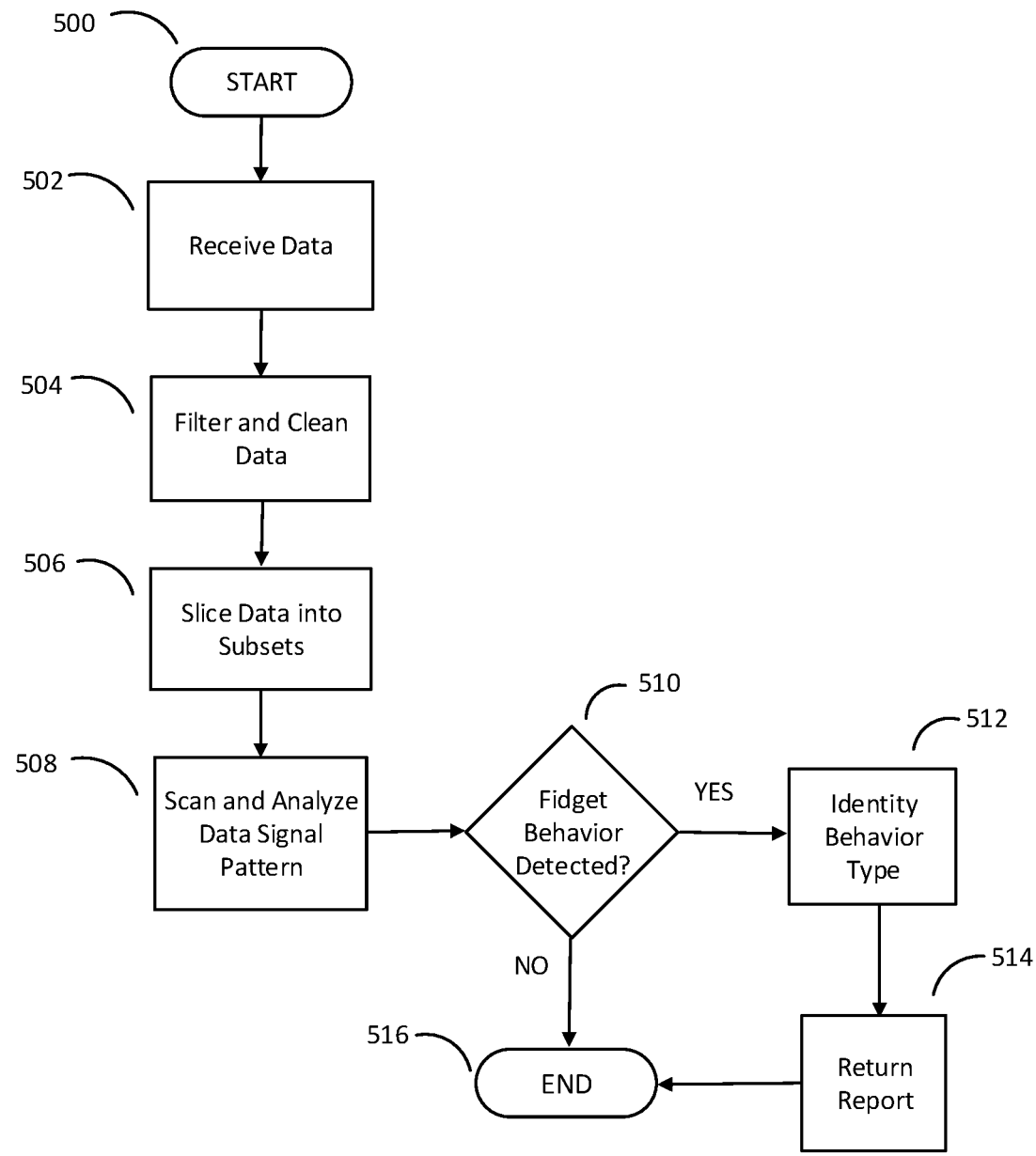
FIG. 5 is an operational flow diagram for a behavior typing sub-process consistent with certain embodiments of the present invention.

Turning now to FIG. 5, an operational flow diagram for a behavior typing sub-process consistent with certain embodiments of the present invention is shown. At 500 the sub-process starts. At 502 the system of the instant innovation receives data input from a user device. Such data may in an embodiment be received from a user-wearable device and may include noise as well as potentially desirable data. At 504 the system of the instant innovation filters and cleans the data, differentiating potentially desirable data from noise. As previously described, the filtering of the data is performed to identify and remove noisy signals that do not contribute to the data, and performs signal analysis to identify weak and/or missing portions of the received signals to strengthen and repair the data signals received by the system. The system retains potentially desirable data in one or more data structures and discards those signals and data fragment which the system determines are noise and not useful data. The retained potential data may be processed by a quantization processor on-board the user device to quantify and normalize the retained data. The output from the quantization processor may then be sent to a base server by any suitable communication method or protocol including, but not limited to, a mobile device employing a Bluetooth module. The base server may be a Lambda Data Base Server, and at 506 the data may be sliced into smaller chunks and the resultant chunked data may be stored on the server. At 508 the system of the instant innovation employs a Machine Learning Algorithm to process the chunked data. In this chunked data processing, the Machine Learning Algorithm scans the chunked data for signal patterns which may be determinative of kinesthetic movement that may be characterized as any cyclic, repetitive non-academically functional behavior associated with conditions such as ADHD, Autism, or other motor-related medical conditions. This kinesthetic movement may, in a non-limiting example, be classified as fidget behavior at 510. The Machine Learning Algorithm may also determine if the identified fidget behavior is fidget behavior that is associated with standing fidget behavior, seated fidget behavior, or a combination of both types of fidget behavior at 512. By way of non-limiting example, fidget behavior so identified may include human kinesthetic behavior such as drumming, jumping, tapping, hopping and/or rocking. At 514 the system of the instant innovation returns a report to an observer in combination with recommendations for ways to improve concentration and on-task behavior by modifying the user's activities to minimize such fidget behavior. At 516 the sub-process ends.

Figure 6:
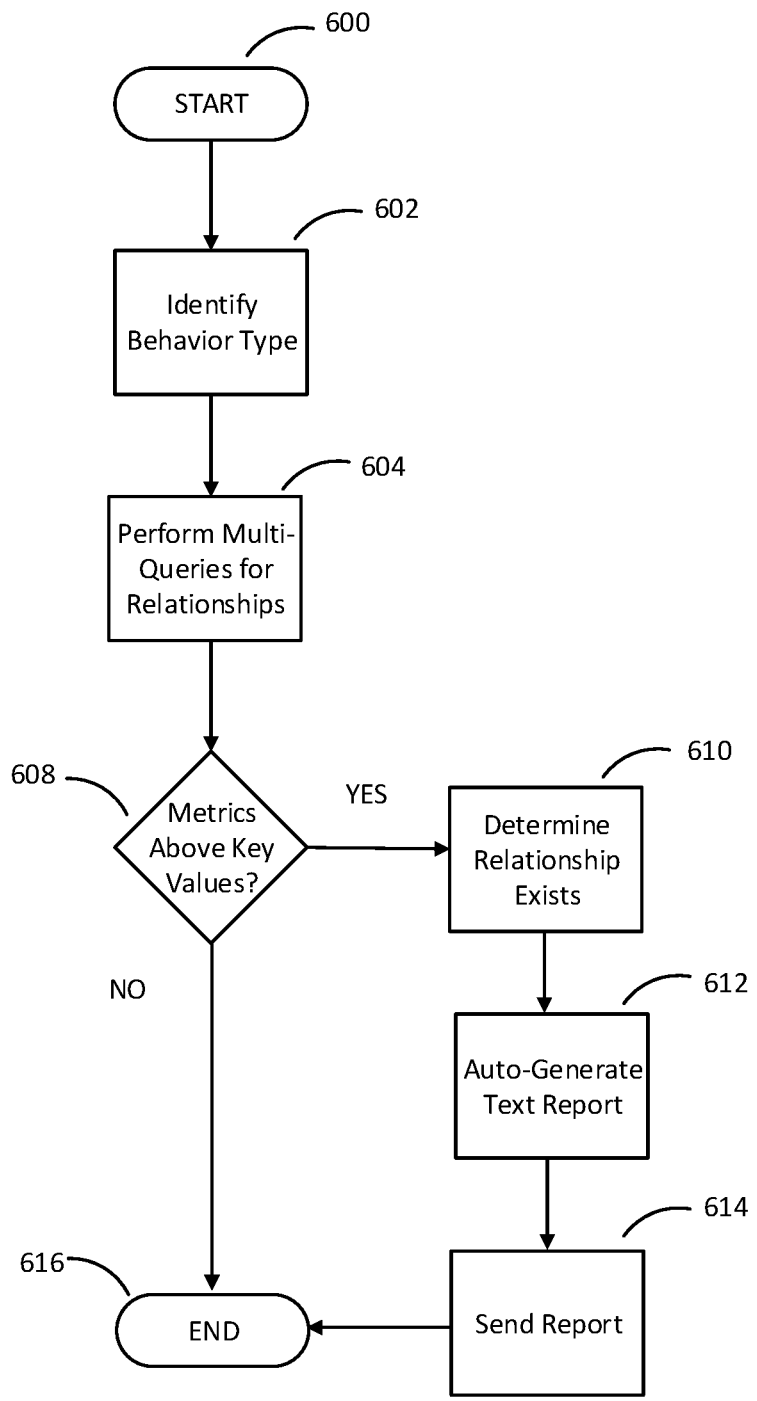
FIG. 6 is an operational flow diagram for a behavior reporting sub-process consistent with certain embodiments of the present invention.

Turning now to FIG. 6, an operational flow diagram for a behavior reporting sub-process consistent with certain embodiments of the present invention is shown. FIG. 6 illustrates more precisely the steps shown at 512 and 514 in FIG. 5. At 600 the sub-process starts. At 602 the system of the instant innovation identifies the type of fidget behavior and whether the behaviors recorded are indicative of seated or standing fidget behaviors. At 604 the system of the instant innovation performs multi-queries for relationships among observed, cleaned, chunked, and identified fidget behavior data. System-performed multi-queries search for relationships between system-identified metrics that are above key P-values. If at 608 the system determines that the identified metrics are above such key P-values, then at 610 the system determines that certain criteria are met to determine the existence of a specific relationship. By way of non-limiting example, a specific relationship could exist (in a statistically significant way) between one user behavior and a desired outcome for another user behavior. Consequently, the instant innovation may calculate one or more insights into connections between, among, and within the user's various behaviors. For instance, the system may be able to determine that a user who takes at least 15,000 steps before lunch experiences measurably improved attention span for the remainder of the day. At 612 the system auto-generates one or more displayable reports intended to convey the existence of the special relationship and may generate one or more insights regarding how the information may be used by the user or an observer and prompting the user to follow the presented recommendation. At 614 the system sends one or more displayable reports, generated as text, video imagery, or other displayable characterization, to an observer who may be the user, a teacher, a clinician, a therapist, or other official observer. In an embodiment such displayable reports may be in other formats including, by way of non-limiting example, audio, visual, or haptic. At 616 the sub-process ends.

While certain illustrative embodiments have been described, it is evident that many alternatives, modifications, permutations and variations will become apparent to those skilled in the art in light of the foregoing description.

We claim:

1. A computer system for behavior modification of a subject with attention-deficit/hyperactivity disorder (ADHD), comprising:
    a data server configured to:
        receive kinesthetic movement data from a wearable device that generates the kinesthetic movement data from movement of a subject;
        analyze the kinesthetic movement data for signal patterns to characterize cyclic, repetitive behavior of the user;
        analyze through an action of one or more computerized computational methods said signal patterns to identify behavioral metrics in said collected data, where said behavioral metrics exceed pre-configured P-values;
        identifying that the behavioral metrics that exceed the P-values satisfy criteria for one or more specific behavioral relationships;
        determining behavioral insights related to the concentration of the subject and the cyclic, repetitive behavior of the subject characterized from the signal patterns; and
        cause a display of one or more actions or recommendations related to concentration of the subject based on one or more of the behavioral insights and the behavioral metrics.

2. The system of claim 1, where the cyclic, repetitive behavior of the user is related to fidget behavior.

3. The system of claim 2, where the fidget behavior is drumming, jumping, tapping, hopping, rocking and/or any cyclic, repetitive non-academically functional behavior associated with ADHD.

4. The system of claim 1, where the calculated insights reflect connections within the user's behaviors.

5. The system of claim 1, where the one or more actions or recommendations are presented in an auto-generated text message.

6. The system of claim 1, where said computerized computational methods comprise a Machine Learning Algorithm operative to analyze received data to identify movement classified as fidget behavior.

7. A method for behavior modification, comprising:
    receiving kinesthetic movement data from a wearable device that generates the kinesthetic movement data from movement of a subject;
    analyzing the kinesthetic movement data for signal patterns to characterize cyclic, repetitive behavior of the user;
    analyzing through an action of one or more computerized computational methods said signal patterns to identify behavioral metrics in said collected data, where said behavioral metrics exceed pre-configured P-values;
    identifying that the behavioral metrics that exceed the P-values satisfy criteria for one or more specific behavioral relationships;
    determining behavioral insights related to the concentration of the subject and the cyclic, repetitive behavior of the subject characterized from the signal patterns; and
    causing a display of one or more actions or recommendations related to concentration of the subject based on one or more of the behavioral insights and the behavioral metrics.

8. The method of claim 7, wherein the cyclic, repetitive behavior of the user is related to fidget behavior.

9. The method of claim 7, where the fidget behavior is drumming, jumping, tapping, hopping, rocking and/or any cyclic, repetitive non-academically functional behavior associated with ADHD.

10. The method of claim 7, where the calculated insights reflect connections within the user's behaviors.

11. The method of claim 7, wherein the returning the behavioral metrics and the calculated insights is in the form of auto-generated text messages.

12. The method of claim 7, where said computerized computational method is a Machine Learning Algorithm operative to analyze received data to identify movement classified as fidget behavior.

* * * * *